US008722862B2

(12) United States Patent
Rossomando et al.

(10) Patent No.: US 8,722,862 B2
(45) Date of Patent: May 13, 2014

(54) REFOLDING TRANSFORMING GROWTH FACTOR BETA FAMILY PROTEINS

(75) Inventors: Anthony Rossomando, South Grafton, MA (US); R. Blake Pepinsky, Arlington, MA (US); BangJian Gong, Andover, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 1544 days.

(21) Appl. No.: 11/573,771

(22) PCT Filed: Aug. 18, 2005

(86) PCT No.: PCT/US2005/029638
§ 371 (c)(1),
(2), (4) Date: Dec. 14, 2007

(87) PCT Pub. No.: WO2006/023782
PCT Pub. Date: Mar. 2, 2006

(65) Prior Publication Data
US 2008/0249287 A1 Oct. 9, 2008

Related U.S. Application Data

(60) Provisional application No. 60/602,825, filed on Aug. 19, 2004.

(51) Int. Cl.
*C07K 1/02* (2006.01)
(52) U.S. Cl.
USPC ......................................................... 530/427
(58) Field of Classification Search
None
See application file for complete search history.

(56) References Cited

U.S. PATENT DOCUMENTS

| | | | |
|---|---|---|---|
| 4,352,883 A | 10/1982 | Lim | |
| 4,353,888 A | 10/1982 | Sefton | |
| 4,407,957 A | 10/1983 | Lim | |
| 4,883,666 A | 11/1989 | Sabel et al. | |
| 4,968,733 A | 11/1990 | Muller et al. | |
| 4,976,859 A | 12/1990 | Wechs | |
| 5,084,350 A | 1/1992 | Chang et al. | |
| 5,158,881 A | 10/1992 | Aebischer et al. | |
| 5,194,596 A | 3/1993 | Tischer et al. | |
| 5,284,761 A | 2/1994 | Aebischer et al. | |
| 5,350,836 A | 9/1994 | Kopchick et al. | |
| 5,414,135 A | 5/1995 | Snow et al. | |
| 5,445,934 A | 8/1995 | Fodor et al. | |
| 5,496,804 A | 3/1996 | Reed et al. | |
| 5,525,464 A | 6/1996 | Drmanac et al. | |
| 5,618,531 A | 4/1997 | Cherksey | |
| 5,641,749 A | 6/1997 | Yan et al. | |
| 5,650,494 A * | 7/1997 | Cerletti et al. | ................ 530/399 |
| 5,654,007 A | 8/1997 | Johnson et al. | |
| 5,733,729 A | 3/1998 | Lipshutz et al. | |
| 5,754,524 A | 5/1998 | Wark | |
| 5,770,577 A | 6/1998 | Kinstler et al. | |
| 5,775,320 A | 7/1998 | Patton et al. | |
| 5,780,014 A | 7/1998 | Eljamal et al. | |
| 5,780,019 A | 7/1998 | Klier et al. | |
| 5,785,049 A | 7/1998 | Smith et al. | |
| 5,795,716 A | 8/1998 | Chee et al. | |
| 5,798,113 A | 8/1998 | Dionne et al. | |
| 5,800,992 A | 9/1998 | Fodor et al. | |
| 5,814,607 A | 9/1998 | Patton | |
| 5,834,029 A | 11/1998 | Bellamkonda et al. | |
| 5,846,935 A | 12/1998 | Panayotatos | |
| 5,916,555 A | 6/1999 | Lee et al. | |
| 5,939,524 A | 8/1999 | Bowditch et al. | |
| 6,063,757 A | 5/2000 | Urso | |
| 6,083,725 A | 7/2000 | Selden et al. | |
| 6,084,076 A * | 7/2000 | Ejima et al. | ................... 530/399 |
| 6,284,540 B1 | 9/2001 | Milbrandt et al. | |
| 6,299,895 B1 | 10/2001 | Hammang et al. | |
| 6,361,771 B1 | 3/2002 | Tao et al. | |
| 6,593,133 B1 | 7/2003 | Johansen et al. | |
| 6,677,135 B1 | 1/2004 | Sanicola-Nadel et al. | |
| 6,723,344 B2 | 4/2004 | Sakiyama-Elbert et al. | |
| 6,734,284 B1 | 5/2004 | Johansen et al. | |
| 7,067,473 B1 | 6/2006 | Masure | |
| 7,115,257 B1 | 10/2006 | Tao et al. | |
| 7,276,580 B2 | 10/2007 | Sah et al. | |
| 7,358,228 B2 | 4/2008 | Sah et al. | |
| 7,442,370 B2 | 10/2008 | Sah et al. | |
| 7,598,059 B2 | 10/2009 | Pederson et al. | |
| 7,601,518 B2 | 10/2009 | Wahlberg et al. | |
| 7,655,463 B2 | 2/2010 | Sah et al. | |

(Continued)

FOREIGN PATENT DOCUMENTS

| | | |
|---|---|---|
| EP | 1 373 503 | 11/2007 |
| EP | 1 930 439 | 6/2008 |

(Continued)

OTHER PUBLICATIONS

Frankel et al. High-Level Expression and Purification of the Recombinant Diphtheria Fusion Toxin DTGM for Phase I Clinical Trials. Protein Expr Purif. Jun. 1999;16(1):190-201.*
Aebischer et al, "Recombinant proteins for neurodegenerative diseases: the delivery issue," Trends in Neuroscience, Elsevier, Amsterdam, NL 24(9):533-540 (2001).
Aebischer et al., "Intrathecal delivery of CNTF using encapsulated genetically modified xenogeneic cells in amyotrophic lateral sclerosis patients," Nature Medicine, 2:696-699 (1996).
Airaksmen et al., GDNF family neurotrophic factor signaling: four masters, one servant, Mol. Cell Neurosci., 13:313-325 (1999).
Alfano et al., "The major determinant of the heparin binding of glial cell-line-derived neurotrophic factor is near the N-terminus and is dispensable for receptor binding," Biochem. J., 404(1):131-40 (2007).
Algvere et al., "Transplantation of RPE in age-related macular degeneration: observations in disciform lesions and dry RPE atrophy," Graefe's Arch. Clin. Exp. Ophthalmol., 235:149-158 (1997).

(Continued)

*Primary Examiner* — Gregory S Emch
(74) *Attorney, Agent, or Firm* — Fish & Richardson P.C.

(57) ABSTRACT

Compositions and methods for folding proteins belonging to the transforming growth factor beta superfamily are disclosed. The compositions and methods allow for the folding of such proteins when produced in an expression system that does not yield a properly folded, biologically active product.

28 Claims, 2 Drawing Sheets

(56) References Cited

U.S. PATENT DOCUMENTS

| | | | |
|---|---|---|---|
| 2002/0002269 A1 | 1/2002 | Milbrandt et al. | |
| 2002/0055467 A1 | 5/2002 | Johansen et al. | |
| 2002/0114780 A1 | 8/2002 | Bankiewicz et al. | |
| 2003/0078373 A1* | 4/2003 | Fersht et al. | 530/350 |
| 2003/0100497 A1 | 5/2003 | Baker et al. | |
| 2003/0166537 A1 | 9/2003 | Hanke | |
| 2003/0186267 A1 | 10/2003 | Feder et al. | |
| 2004/0028613 A1 | 2/2004 | Quay | |
| 2004/0077543 A1 | 4/2004 | Sah et al. | |
| 2004/0142418 A1 | 7/2004 | Sah et al. | |
| 2004/0230043 A1 | 11/2004 | Johansen et al. | |
| 2004/0242472 A1 | 12/2004 | Shelton et al. | |
| 2004/0265972 A1 | 12/2004 | Weintraub et al. | |
| 2005/0069520 A1 | 3/2005 | Shi et al. | |
| 2005/0089960 A1 | 4/2005 | Wahlberg et al. | |
| 2005/0118157 A1 | 6/2005 | McMahon et al. | |
| 2005/0142098 A1 | 6/2005 | Sah et al. | |
| 2005/0158824 A1 | 7/2005 | Pedersen et al. | |
| 2005/0180957 A1 | 8/2005 | Scharp et al. | |
| 2005/0181991 A1 | 8/2005 | Shelton et al. | |
| 2005/0233359 A1 | 10/2005 | Masure et al. | |
| 2006/0009625 A1 | 1/2006 | Bedows et al. | |
| 2006/0014288 A1 | 1/2006 | Kim et al. | |
| 2006/0122135 A1 | 6/2006 | Geerts et al. | |
| 2007/0238650 A1 | 10/2007 | Sah et al. | |
| 2007/0254842 A1 | 11/2007 | Bankiewicz | |
| 2008/0039385 A1 | 2/2008 | Rossomando et al. | |
| 2008/0227703 A1 | 9/2008 | Johansen et al. | |
| 2008/0249287 A1 | 10/2008 | Rossomando et al. | |
| 2008/0260702 A1 | 10/2008 | Jorgensen | |
| 2008/0306212 A1 | 12/2008 | Sah et al. | |
| 2009/0221495 A1 | 9/2009 | Rossomando et al. | |
| 2009/0258831 A1 | 10/2009 | Sah | |
| 2010/0056440 A1 | 3/2010 | Rossomando et al. | |
| 2010/0261654 A1 | 10/2010 | Rossomando et al. | |
| 2010/0292142 A1 | 11/2010 | Sah et al. | |

FOREIGN PATENT DOCUMENTS

| | | |
|---|---|---|
| JP | 11-310600 | 11/1999 |
| JP | 2002-534957 | 10/2002 |
| JP | 2003-310258 | 11/2003 |
| WO | WO 92/19195 | 11/1992 |
| WO | WO 93/06116 | 4/1993 |
| WO | WO 95/05452 | 2/1995 |
| WO | WO 97/08196 | 3/1997 |
| WO | WO 97/11964 | 4/1997 |
| WO | WO 97/19693 | 6/1997 |
| WO | WO 98/32869 | 7/1998 |
| WO | WO 99/03887 | 1/1999 |
| WO | WO 99/13090 | 3/1999 |
| WO | WO 99/42486 | 8/1999 |
| WO | WO 99/43813 | 9/1999 |
| WO | WO 99/49039 | 9/1999 |
| WO | WO 00/01815 | 1/2000 |
| WO | WO 00/04050 | 1/2000 |
| WO | WO00/15665 | 3/2000 |
| WO | WO 00/18799 | 4/2000 |
| WO | WO 00/34475 | 6/2000 |
| WO | WO 00/73348 | 12/2000 |
| WO | WO 01/47946 | 7/2001 |
| WO | WO 01/53486 | 7/2001 |
| WO | WO01/66164 | 9/2001 |
| WO | WO01/76639 | 10/2001 |
| WO | WO01/87925 | 11/2001 |
| WO | WO 02/46430 | 6/2002 |
| WO | WO 02/051433 | 7/2002 |
| WO | WO 02/060929 | 8/2002 |
| WO | WO 02/072826 | 9/2002 |
| WO | WO 02/078730 | 10/2002 |
| WO | WO03/044055 | 5/2003 |
| WO | WO 2004/002763 | 1/2004 |
| WO | WO 2004/069176 | 8/2004 |
| WO | WO 2004/094592 | 11/2004 |
| WO | WO 2004/108760 | 12/2004 |
| WO | WO 2005/039643 | 5/2005 |
| WO | WO 2006/023781 | 3/2006 |
| WO | WO 2006/023782 | 3/2006 |
| WO | WO 2007/042040 | 4/2007 |
| WO | WO 2007/100898 | 9/2007 |
| WO | WO 2007/103182 | 9/2007 |
| WO | WO 2008/137574 | 11/2008 |
| WO | WO 2009/020964 | 2/2009 |

OTHER PUBLICATIONS

Anderson, "Human gene therapy," Nature, 392:25-30 (1998).

Andres et al., "Multiple effects of artemin on sympathetic neurone generation, survival and growth," Development 128:3685-3695 (2001).

Atschul et al., "Gapped BLAST and PSI-BLAST: a new generation of protein database search programs," Nucl. Acids Res., 25:3389-3402 (1997).

Baloh et al. "Artemin, a novel member of the GDNF ligand family, supports peripheral and central neurons and signals through the GFRalpha3-RET receptor complex," Neuron, 21(6):1291-1302 (1998).

Baloh et al., "Functional mapping of receptor specificity domains of glial cell line-derived neurothropic factor (GDNF) family ligands and production of GFR alpha 1 RET-specific agonists," J. of Biological Chemistry, 275(5):3412-3420 (2000).

Baudet et al., "Positive and negative interactions of GDNF, NTN and ART in developing sensory neuron subpopulations, and their collaboration with neurotrophins," Development, 127:4335-4344 (2000).

Bauskin et al., "The propeptide of macrophage inhibitory cytokine (MIC-1), a TGF-β superfamily member, acts as a quality control determinant for correctly folded MIC-1," The EMBO Journal, 19(10):2212-2220 (2000).

Bendtsen et al., "Improved prediction of signal peptides—SignalP 3.0," J. Mol. Biol., 340(4):783-795 (2004).

Bonde et al., "GDNF and neublastin protect against NMDA-induced excitotoxicity in hipocampal slice cultures," Neuroreport., 11:4069-4073 (2000).

Bootcov et al., "MIC-1, a novel macrophage inhibitory cytokine, is a divergent member of the TGF-β superfamily," Pro. Natl. Acad. Sci. U.S.A., 94:11514-11519 (1997).

Bork, "Go hunting in sequence databases but watch out of the traps," Trends in Genetics, 12:425-427 (1996).

Bork, "Powers and Pitfalls in Sequence analysis: the 70% Hurdle," Genome Research, 10:398-400 (2000).

Borodovsky et al., "Detection of new genes in a bacterial genome using Markov models for three gene classes," Nucl. Acids Res., 23:3554-3562 (1995).

Boucher et al "Artemin prevents injury-induced changes in small sensory neurons," Abstracts of the Society for Neuroscience, Society for Neuroscience, Washington D.C. 26(1/2):63305 (2000).

Brenner, "Errors in genome annotation," Trends in Genetics, 15:132-133 (1999).

Burgess et al., "Possible dissociation of the heparin-binding and mitogenic activities of heparin-binding (acidic fibroblast) growth factor-1 from its receptor-binding activities by site-directed mutagenesis of a single lysine residue," J. of Cell Biology, 111:2129-2138 (1990).

Callister et al., Soc. for Neuroscience Abstracts 27(1):36.11 (2001).

Campbell et al., "Mechanisms of Neuropathic Pain," Neuron, 52:77-92 (2006).

Carmillo et al., "Glial Cell Line-Derived Neurotrophic Factor (GDNF) Receptor α-1(GFRα1) Is Highly Selective for GDNF versus Artemin," Biochemistry, 44:2545-2554 (2005).

Ceyhan et al., "The neurotrophic factor artemin influences the extent of neural damage and growth in chronic pancreatitis," Gut., 56(4):534-44 (2007).

Daopin et al., "Crystal structure of TGF-β2 refined at 1.8 A resolution," Proteins, 17:176-192 (1993).

Delgado et al., "The uses and properties of PEG-Linked proteins," Critical Reviews in Therapeutic Drug Carrier Systems, 9(3/4):249-304 (1992).

(56) References Cited

OTHER PUBLICATIONS

Doerks et al., "Protein annotation: detective work for function prediction," Trends in Genetics, 14:248-250 (1998).
During et al., "Towards gene therapy for the central nervous system," Mol. Med., 11:485-493 (1998).
Eigenbrot et al., "X-ray structure of glial cell-derived neurotrophic factor at 1 9 A resolution and implications for receptor binding," Nat. Struct. Biol., 4:435-438 (1997).
Enomoto et al., "RET signaling is essential for migration, axonal growth and axon guidance of developing sympathetic neurons," Development, 128:3963-3974 (2001).
Enzmann et al., "Immunological problems of transplantation into the subretinal space," Acta Anat., 162:178-183 (1998).
Fairlie et al., "The propeptide of the transforming growth factor-β superfamily member, macrophage inhibitory cytokine-1 (MIC-1), is a multifunctional domain that can facilitate protein folding and secretion," J. of Biol. Chem., 276(20):16911-16918 (2001).
Finsen et al., "Somatostatin and neuropeptide Y in organotypic slice cultures of the rat hippocampus: an immunocytochemical and in situ hybridization study," Neurosci., 47:105-113 (1992).
Fjord-Larsen, et al. "Efficient in vivo protection of nigral dopaminergic neurons by lentiviral gene transfer of a modified Neurturin construct," Experimental Neurology, 195:49-60 (2005).
Flanders et al., "TGFβ," Laboratory of Cell Regulation and Carcinogenesis, National Cancer Institute, 719-746, 2000.
Francis et al., "Pegylation of Cytokines and other therapeutic proteins and peptides: the importance of biological optimization of coupling techniques," Int'l. Journal of Hematology, Elsevier Science Publishers, NL., 68(1):1-18 (1998).
Friedmann, "Principles for human gene therapy studies," Science, 287:2163-2164 (2000).
Gardell et al., "Multiple actions of systemic artemin in experimental neuropathy," Nat Med., 9(11):1383-89 (2003).
GenBank Accession No. AA844072, 2 pages (1998).
GenBank Accession No. AC005037, Waterston, 54 pages (1998).
GenBank Accession No. AC005038, Sulston et al., 96 pages (2001).
GenBank Accession No. AC005051, Waterston, 38 pages (1998).
GenBank Accession No. AF040962, Milbrandt et al., 2 pages (1998).
Genbank Accession No. AF120274, Rosenblad et al., 3 pages (1999).
Gilchuk, "Assessment of renaturation methods for industrial producing recombinant proteins in biologically active form from *E.coli* inclusion bodies," Biopolymers and Cell, 20(3):182-192 (2004).
Griffin et al., "Assessment of cutaneous innervation by skin biopsies," Current Opinion in Neurology, 14:655-659 (2001).
Gustafsson, "New insights in oestrogen receptor (ER) research—the ERbeta," Eur. J. Cancer, 36 Suppl. 4:S16 (2000).
Hall et al., "Eukaryotic and Prokaryotic Signal Peptides Direct Secretion of a Bacterial Endoglucanase by Mammalian Cells," Journal of Biological Chemistry, 265(32):19996-19999 (1990).
Hallböök et al., "Expression of Neurotrophins and Trk Receptors in the Avian Retina," J. Compar. Neurol., 364:664-676 (1996).
Hamilton et al., "Heparin coinfusion during convection-enhanced delivery (CED) increases the distribution of the glial-derived neurotrophic factor (GDNF) ligand family in rat striatum and enhances the pharmacological activity of neurturin," Experimental Neurology, 168:155-161 (2001).
Hoane et al. "Mammalian-Cell-Produced Neurturin (NTN) Is More Potent Than Purified *Escherichia coli*-Produced NTN," Exp. Neurol., 162:189-193 (2000).
Israel et al., "Acetylcholine Release and the Cholinergic Genomic Locus," Molecular Neurobio., 16(1):1-20 (1998).
Johansen et al., "Biosynthesis of peptide precursors and protease inhibitors using new consititutive and inducible eukaryotic expression vectors," FEBS Lett., 267:289-294 (1990).
Kim et al., "An experimental model for peripheral neuropathy produced by segmental spinal nerve ligation in the rat," Pain, 50:355-363 (1992).
Kirsch et al. "Expression of ciliary neurotrophic factor receptor mRNA and protein in the early postnatal and adult rat nervous system," Neurosci. Lett., 180:163-166 (1994).

Lapchak et al., "Pharmacological characterization of glial cell line-derived neurotrophic factor (GDNF): implications for GDNF as a therapeutic molecule for treating neurodegenerative diseases," Cell Tissue Res., 286:179-189 (1996).
Lapchak, "Therapeutic potential for glial cell line-derived neurotropic factor (GDNF) based upon pharmacological activities in the CNS," Rev. Neurosci., 7:165-176 (1977).
Lavail et al., "Protection of mouse photoreceptors by survival factors in retinal degenerations," Invest. Ophthalmol. Vis. Sci., 39(3):592-602 (1998).
Lee et al., "Proliferin Secreted by Cultured Cells Binds to Mannose 6-Phosphate", J. Biol. Chem., 263(7):3521-3527 (1988).
Li et al., "beta-Endorphin omission analogs: dissociation of immunoreactivity from other biological activities," PNAS, 77(6):3211-14 (1990).
Li et al., "Expression, purification, and characterization of recombinant human neurturin secreted from the yeast *Pichia pastoris*," Protein Expression and Purification, 30(1):11-17 (2003).
Lin et al., "GDNF: A glial cell line-derived neurotrophic factor for midbrain dopaminergic neurons," Science, 260:1130-1132 (1993).
Little et al., "Transplantation of human fetal retinal pigment epithelium rescues photoreceptor cells from degeneration in the royal college of surgeons rat retina," Invest. Ophthalmol. Vis. Sci., 37(1):204-211 (1996).
Lorenz et al., "Heteromultimeric CLC chloride channels with novel properties," Proc. Natl. Acad. Sci USA, 93:13362-13366 (1996).
Maeda et al., "Efficient Production of Active TNF α By albumin Signal Peptide," Biochemistry and Molecular Biology International, Academic Press, London, GB, 42(4):825-832 (1997).
Massague et al., "The Tgf-β family and its composite receptor," Trends Cell Biol., 4:172-178 (1994).
Masure et al., "Enovin, a novel member of the GDNF family of neurotrophic growth factors with growth promoting and neuroprotective effects on neuronal cells," a poster presentation from Janssen Research Foundation, "Gordon Conference" held on Jun. 6-11, 1999.
Masure, et al., "Enovin, a member of the glial cell-line-derived neurotrophic factor (GDNF) family with growth promoting activity on neuronal cells," Eur J. Biochem., 266:892-902 (1999).
Matsushita et al., "Cloning and structural organization of the gene encoding the mouse glial cell line-derived neurotrophic factor, GDNF," Gene, 203:149-157 (1997).
McDonald et al., "A structural superfamily of growth factors containing a cystine knot motif.," Cell, 73:421-424 (1993).
Merlo et al. "The Mouse *int*-2 Gene Exhibits Basic Fribroblast Growth Facctor Activity in a Basic Fibroblast Growth Factor-responsive Cell Line," Cell Growth & Differentiation, 1:463-472 (1990).
Milbrandt et al., "Persephin, a novel neurotrophic factor related to GDNF and Neurturin," Neuron, 20:245-253 (1998).
Moustakas et al., "Smad regulation in TGF-β signal transduction," J. of Cell Science, 114:4359-4369 (2001).
Ngo et al., "The Protein Folding Problem and Tertiary Structure Prediction," Birkhäuser, 492-495 (1994).
Nielsen et al., "Identification of prokaryotic and eukaryotic signal peptides and prediction of their cleavage sites," Protein Engineering, 10(1):1-6 (1997).
Nielsen et al., "Prediction of signal peptides and signal anchors by a hidden Markov model," Proceedings of the 6th International Conference on Intelligent systems for Molecular Biology, 122-130 (1998).
Nishino et al., "GFR alpha3, a component of the artemin receptor, is required for migration and survival of the superior cervical ganglion," Neuron, 23(4):725-736 (1999).
Norton et al., "Bacterial beta-Galactosidase as a Marker of Rous Sarcoma Virus Gene Expression and Replication," Mol. Cell. Biol., 5:281-290 (1985).
Orozco et al., "Nociceptive Neurons Express GFRα3," Society for Neuroscience, Abstracts 26 (1-2): Abstract No. 412.7 (2000).
Orozco et al., "GFRalpha3 is expressed predominantly in nociceptive sensory neurons," Eur. J. Neurosci., 13(11):2177-82 (2001).
Palmiter, "Heterologous introns can enhance expression of transgenes in mice," PNAS, 88:478-482 (1991).
Pawson et al., "Assembly of cell regulatory systems through protein interaction domains," Science, 300:445-452 (2003).
Pir_80 Accession No. 14968, 1996.

(56) References Cited

OTHER PUBLICATIONS

Rakowicz et al., "Glial Cell Line-Derived Neurotrophic Factor Promotes the Survival of Early Postnatal Spinal Motor Neurons in the Lateral and Medial Motor Columns in Slice Culture," The Journal of Neuroscience, 22(10):3953-3962 (2002).
Rattenholl et al., "Pro-sequence assisted folding and disulfide bond formation of human nerve growth factor," J. Mol. Biol., 305:523-533 (2001).
Rattenholl et al., "The pro-sequence facilitates folding of human nerve growth factor from Escherichia coli inclusion bodies," Eur. J. Biochem., 268:3296-3303 (2001).
Reddy, "Controlled-release peylation, liposomal formulations: new mechanisms in the delivery of injectable drugs," Annals of Pharmacotherapy, 34(7/8):915-923 (2000).
Reinshagen et al., "Commercial recombinant human β-Nerve Growth factor and adult rat dorsal root ganglia contain an identical molecular species of nerve growth factor prohormone," J. of Neurochemistry, 74:2127-2133 (2000).
Riganti et al., "Nitroarginine methyl ester and canavanine lower intracellular reduced glutathione," Free Radic. Biol. Med., 35(10):1210-6 (2003).
Robertson et al., "The GDNF-RET signaling in partnership," Trends Genet., 13:1-3 (1997).
Rosenberg et al., "Gene therapist, heal thyself," Science, 287:1751 (2000).
Rosenberg et al., "Vectors for selective expression of cloned DNAs by T7 RNA polymerase," Gene, 56:125-135 (1987).
Rosenblad et al., "In vivo protection of nigral dopamine neurons by lentiviral gene transfer of the novel GDNF-family member neublastin/artemin," Molecular and Cellular Neuroscience, 15(2):199-214 (2000).
Rosenblad et al., "In vivo protection of nigral dopamine neurons by lentiviral gene transfer of the novel GDNF-family member neublastin/artemin," Mol. Cell Neurosci., 18(3):332-333 (2001).
Saarma et al., "Other neurotrophic factors: glial cell line-derived neurotrophic factor (GDNF)," Microsc. Res. Tech., 45(4-5):292-302 (1999).
Saarma, "GDNF: A stranger in the TGF-beta superfamily?" European Journal of Biochemistry, 267(24):6968-6971 (2000).
Sadick et al., "Analysis of heregulin-induced ErbB2 phosphorylation with a high-throughput Kinase receptor activation enzyme-linked immunosorbant assay," Anal. Biochem., 235(2):207-14 (1996).
Sah et al., "Prevention and Reversal of Experimental Neuropathic Pain by Systemic Neublastin," Society for Neuroscience Abstracts, 27(1):361 (2001).
Sanicola et al., "Glial cell line-derived neurotrophic factor-dependent RET activation can be mediated by two different cell-surface accessory proteins," Proc Natl Acad Sci, USA, 94:6238-6243 (1997).
Sauer et al., "Progressive degeneration of nigrostriatal dopamine neurons following intrastraiatal terminal lesions with 6-hydroxydopamine: a combined retrograde tracing and immunocytochemical study in the rat," Neuroscience, 59:401-415 (1994).
Schmidt et al. "In vivo kinetics as a sensitive method for testing physiologically intact human recombinant apolipoprotein A-1: comparison of three different expression systems," Clinica Chimica Acta, 268(1-2):41-60 (1997).
Skolnick et al. "From genes to protein structure and function: novel applications of computational approaches in the genomic era," Trends in Biotech., 18(1):34-39 (2000).
Sloot et al., "Detection of salicylate and its hydroxylated adducts 2.3- and 2.5-dihydroxybenzoic acids as possible indices for in vivo hydroxyl radical formation in combination with catechol- and indoleamines and their metabolites in cerebrospinal fluid and brain tissue," J. Neurosci. Meth., 60:141-149 (1995).
Smith et al. "The challenges of genome sequence annotation" or "The devil is in the details," Nature Biotechnology, 15:1222-1223 (1997).
Stoppini et al., "A simple method for organotypic cultures of nervous tissue," J. Neurosci. Methods, 37:173-182 (1991).
Thompson et al., "The ClustalX windows interface: flexible strategies for multiple sequence alignment aided by quality analysis tools," Nucl. Acids Res., 25:4876-4882 (1997).
Tseng et al., "Neurturin protects dopaminergic neurons following medial forebrain bundle axotomy," Mol. Neurosci, 9:1817-1822 (1998).
Unsicker, "GDNF: a cytokine at the interface of TGF-betas and neurotrophins," Cell Tissue Res., 286:175-178 (1996).
Vallejo et al., "Optimized procedure for renaturation of recombinant human bone morphogenetic protein-2 at high protein concentration," Biotechnol. Bioeng., 85(6):601-609 (2004).
Varmus, "Gene therapy: Not ready for prime time," Nature Medicine, 2(1):7-8 (1996).
Verma et al., "Gene therapy—promises, problems and prospects," Nature, 389:239-242 (1997).
Verma, "Gene therapy: beyond 2000," Mol. Ther., 6:493 (2000).
Veronese et al., "Introduction and Overview of Peptide and Protein Pegylation," Advanced Drug Delivery Reviews, 54(4):453-456 (2002).
Von Schwedler et al., "Vif is crucial for human immunodeficiency virus type 1 proviral DNA synthesis in infected cells," J. Virol., 67:4945-4955 (1993).
Vukicevic et al., "Induction of nephrogenic mesenchyme by osteogenic protein 1 (bone morphogenetic protein 7)," PNAS USA, 93:9021-9026 (1996).
Wang et al., "Animal and cellular models of chronic pain ," Adv. Drug Delivery Rev., 55:949-965 (2003).
Wang et al , "Inhibitory effect of endostatin expressed by human liver carcinoma SMMC7721 on endothelial cell proliferation in vitro," World Journal of Gastroenterology, 8(2):253-257 (2002).
Watabe et al., "Spontaneously immortalized adult mouse Schwann cells secrete autocrine and paracrine growth-promoting activities," J. Neurosci. Res., 41:279-90 (1995).
Wefstaedt et al., "Neurotrophic factors of the GDNF family and their receptors are detectable in spiral ganglion cells of normal hearing as well as of deafened rats," Laryngorhinootologie, 85(11):802-8 (2006) (English abstract only, see p. 807).
Wells, "Additivity of Mutational Effects in Proteins," Biochemistry, 29:8509-8517 (1990).
West et al., "Estimation of the Number of Somatostatin Neurons in the Striatum: An In Situ Hybridization Study Using the Optical Fractionator Method," J. Comp. Neurol., 370:11-22 (1996).
White et al., "Chemokines: integrators of pain and inflammation," Nat Rev. Drug discovery 4:834-844 (2005).
Zufferey et al., "Multiply attenuated lentiviral vector achieves efficient gene delivery in vivo," Nat. Biotechnol., 15:871-875 (1997).
Abrams et al., "Emerging strategies to promote improved functional outcome after peripheral nerve injury," Restor. Neurol. Neurosci., 23(5-6):367-82 (2005).
Anonymous, "Anti-human Artemin Antibody," R&D Systems Product Data Sheets (Dec. 27, 2006), [online] XP002505114. Retrieved from the Internet: http://www.rndsystems.com/pdf/AF2589.pdf [retrieved on Nov. 21, 2008].
Anonymous, "Monoclonal Anti-human Artemin Antibody," R&D Systems Product Data Sheets (Mar. 23, 2006), [online] XP002505115. Retrieved from the Internet: http://www.rndsystems.com/pdf/MAB2589.pdf [retrieved on Nov. 21, 2008].
Bennett et al., "A distinct subgroup of small DRG cells express GDNF receptor components and GDNF is protective for these neurons after nerve injury," J. Neurosci. 18(8):3059-3072 (Apr. 15, 1998).
Bennett et al., "Artemin has potent neurotrophic actions on injured C-fibres," J. Peripher. Nerv. Syst., 11(4):330-45 (2006).
Bennett, G., "An animal model of neuropathic pain: A review," Muscle & Nerve 16:1040-1048 (1993).
Ceyhan et al., "The neurotrophic factor artemin promotes pancreatic cancer invasion," Ann. Surg., 244:274-81 (2006).
Damon et al., "Vascular-derived artemin: a determinant of vascular sympathetic innervation?," Am. J. Physiol. Heart Circ. Physiol., 293:H266-H273 (2007).
Freynhagen et al., "The evaluation of neuropathic components in law back pain," Current Pain & Headache Reports 13:185-190 (2009).

(56) References Cited

OTHER PUBLICATIONS

Guerra et al., "PEGylation prevents the N-terminal degradation of megakaryocyte growth and development factor," Pharm. Res., 15(12):1822-1827 (1998).
Kotzbauer et al., "Neurturin, a relative of glial-cell-line-derived neurotrophic factor," Nature, 384:467-70 (1996).
Kron et al., "Coronary revascularization rather than cardiac transplantation for chronic ischemic cardiomyopathy," Ann. Surg., 210:348-352 (1989).
Lee et al., "Prolonged circulating lives of single-chain Fv proteins conjugated with polyethylene glycol: a comparison of conjugation chemistries and compounds," Bioconjug. Chem., 10:973-981 (1999).
Machelska et al., "Breaking the pain barrier," Nature Medicine 9(11):1353-1354 (2003).
Mason, "The RET receptor tyrosine kinase: activation, signalling and significance in neural development and disease," Pharm. Acta. Helv., 74:261-4 (2000).
Masure et al., "Mammalian GFRalpha -4, a divergent member of the GFRalpha family of coreceptors for glial cell line-derived neurotrophic factor family ligands, is a receptor for the neurotrophic factor persephin," J. Biol. Chem., 275:39427-34 (2000).
Mogyoros et al., "Strength-duration properties of sensory and motor axons in amyotrophic lateral sclerosis," Brain 121:851-859 (1998).
Moore et al., "Renal and neuronal abnormalities in mice lacking GDNF," Nature, 382:76-79 (1996).
Park et al., "Coordinated interaction of the vascular and nervous systems: from molecule- to cell-based approaches," Biochem. Biophys. Res. Commun., 311:247-253 (311) (2003).
Pons et al., "Massive cortical reorganization after sensory deafferentation in adult macaques," Scient. 252(5014):1857-1860 (1991).
Ramachandran et al., "Perceptual correlates of massive cortical reorganization," Science 258(5085):1159-1160 (1992).
Ramachandran, "Behavioral and MEG correlates of neural plasticity in the adult human brain," Proceedings of the National Academy of Sciences 90:10413-10420 (1993).
Rico et al., "Characterization of the immunostimulatory properties of Leishmania infantum HSP70 by fusion to the *Escherichia coli* maltose-binding protein in normal and nu/nu BALB/c mice," Infect Immun. 66:1347-352 (Jan. 1998).
Rossomando et al., "In vitro and in vivo characterization of neublastin, a nociceptive neuronal trophic factor," Abstracts of the Annual Meeting of the Society for Neuroscience, Society for Neuroscience, Washington, DC, U.S., 27(1):361 (2001) (XP001121851, ISSN: 0190-5295).
Sah et al., "Neurotrophic factors as novel therapeutics for neuropathic pain," Nature Reviews 2:460-472 (2003).
Sah et al., "New approaches for the treatment of pain: the GDNF family of neurotrophic growth factors," Curr. Top Med. Chem., 5(6):577-83 (2005).
Silvian, L. et al., "Artemin crystal structure reveals insights into heparan sulfate binding," Biochemistry 45(22):6801-12 (Jun. 2006).
Snider et al., "Tackling pain at the source: new ideas about nociceptors," Neuron 20:629-632 (Apr. 1998).
Trupp et al., "Peripheral expression and biological ctivities of GDNF, a new neurotrophic factor for avian and mammalian peripheral neurons," The Journal of Cell Biology 130(1):137-148 (Jul. 1995).
Vickers, "A vaccine against Alzheimer's disease: developments to date." Drugs Aging 19(7):487-94 (2002).
Wang et al., "Persistent Restoration of sensory function by immediate or delayed systemic artemin after dorsal root injury," Nature Neurosci. 11(4):488-496 (2008).
Wang et al., "Single-chain Fv with manifold N-glycans as bifunctional scaffolds for immunomolecules," Protein Eng., 11(12):1277-83 (1998).
Yan, M. et al., "Two-amino acid molecular switch in an epithelial morphogen that regulates binding to two distinct receptors," Science 290:523-527 (2000).
Accession No. AF109402 (1998).
Airaksinen et al., "The GDNF family: signalling, biological functions and therapeutic value," Nature Reviews, Neuroscience 3:383-394 (May 2002).
Honma et al., "Artemin is a vascular-derived neurotrophic factor for developing sympathetic neurons," Neuron 35(2):267-282 (2002).
Mills, C.D. et al., "Strain and model differences in behavioral outcomes after spinal cord injury in rat," J. Neurotrauma 18(8):743-56, 2001.
Park et al., "Tamscriptional regulation of artemin is related to neurite outgrowth and actin polymerization in mature DRG neurons," Neuroscience Letters 404:61-66 (2006).
Purves, D. et al.; "The Cover, Dorsal view of the human brain," Neuroscience, Sinauer Associates, Inc., 2nd Ed., pp. 75, 367, 400, 403, 554, 555, and 678, 2001.
Ramer et al., "Functional regeneration of sensory axons into the adult spinal cord," Nature 403:312-316 (Jan. 2000).
Stokes, B.T. et al., "Experimental modeling of human spinal cord injury: a model that crosses the species barrier and mimics the spectrum of human cytopathology," Spinal Cord 49:101-109, 2002.
Talac, R. et al., "Animal models of spinal cord injury for evaluation of tissue engineering treatment strategies," Biomaterials 25:1505-1510, 2004.

\* cited by examiner

| | | |
|---|---|---|
| Huneublastin | (1) | MGHHHHHHHHHHSSGHIDDDDKAGGPGSRARAAGARGCRLRSQLVPVRAL |
| rneublastin | (1) | MGHHHHHHHHHHSSGHIDDDDKAGTRSSRARATDARGCRLRSQLVPVSAL |
| Huneublastin | (51) | GLGHRSDELVRFRFCSGSCRRARSPHDLSLASLLGAGALRPPPGSRPVSQ |
| rneublastin | (51) | GLGHSSDELIRFRFCSGSCRRARSPHDLSLASLLGAGALRSPPGSRPISQ |
| Huneublastin | (101) | PCCRPTRYEAVSFMDVNSTWRTVDRLSATACGCLG (SEQ ID NO:2) |
| rneublastin | (101) | PCCRPTRYEAVSFMDVNSTWRTVDHLSATACGCLG (SEQ ID NO:3) |

Fig. 1

REFOLDING TRANSFORMING GROWTH FACTOR BETA FAMILY PROTEINS

CROSS REFERENCE TO RELATED APPLICATIONS

This application is a national phase filing under 35 U.S.C. 371 of international application number PCT/US2005/029638, filed Aug. 18, 2005, which claims priority from provisional application No. 60/602,825, filed Aug. 19, 2004. The entire content of the prior applications are incorporated herein by reference in their entirety.

TECHNICAL FIELD

The invention relates to compositions and methods for refolding proteins belonging to the transforming growth factor beta superfamily.

BACKGROUND

Neublastin, also known as Artemin and Enovin, is a 24-kDa homodimeric secreted protein that promotes the survival of neurons of the peripheral and central nervous system such as dopaminergic neurons (Baudet et al., 2000, *Development*, 127:4335; Roseblad et al., 2000, *Mol. Cell Neurosci.*, 15(2):199; GenBank™ AF120274). The gene encoding neublastin has been cloned and sequenced (Roseblad et al., 2000, *Mol. Cell Neurosci.*, 15(2):199; Baloh et al., *Neuron*, 21:1291).

Neublastin is a member of the glial cell line-derived neurotrophic factor (GDNF) ligand family. At the cellular level, GDNF members activate the receptor tyrosine kinase, RET. RET associates with a co-receptor, GDNF family receptor α (GFRα), a glycosylphosphatidyl inositol (GPI) linked membrane protein that provides ligand specificity for RET. Four GFRα's are known (GFRα1-4). Neublastin binds to GFRα3 together with RET forming a ternary signaling complex (Baudet et al. 2000, *Development*, 127:4335; Baloh et al., 1998, *Neuron*, 21:1291), which is localized predominantly on nociceptive sensory neurons (Orozco et al., 2001, *Eur. J. Neurosci.*, 13(11):2177). These neurons detect pain and injury. Thus, neublastin has clinical application in the general treatment of neuropathy and more specifically in the treatment of neuropathic pain.

Neublastin and the other GDNF family members are members of the transforming growth factor beta (TGF beta) superfamily and thus, are characterized by the presence of seven conserved cysteine residues with similar spacing which form the structure of a cysteine knot (Saarma, 1999, *Microsc. Res. Tech.*, 45:292). Each monomer contains two disulfide bonds that form a closed loop structure encircling the third disulfide to form a tight knot structure. The seventh cysteine contained within each monomer forms an intermolecular disulfide bond, covalently linking the monomers to form the final dimer product (Rattenholl et al 2000, *J. Mol. Biol.*, 305:523).

TGF beta family members are synthesized as pre pro proteins that eventually are secreted as a mature homodimer after cleavage of the signal peptide and pro-domain (see e.g. Rattenholl, et al., 2000, *J. Mol. Biol.*, 305:523; Fairlie et al., 2001, *J. Biol. Chem.*, 276(20):16911). Both the signal peptide and pro-domain mediate proper secretion for TGF beta family members (Rattenholl et al., 2000, *J. Mol. Biol.*, 305:523; Rattenholl et al., 2001, *Eur. J. Biochem.*, 268:3296).

SUMMARY

The invention is based, at least in part, on the discovery that certain buffer compositions are particularly effective at inducing the refolding of a denatured polypeptide. The compositions and methods detailed herein were developed to induce protein refolding, so as to result in a polypeptide having a proper three dimensional structure and accompanying biological activity.

In one aspect, the invention features a method of inducing folding of a denatured polypeptide by: (1) providing a denatured polypeptide; and (2) contacting the polypeptide with an amount of a refolding buffer effective to induce folding of the polypeptide, wherein the refolding buffer contains (i) potassium phosphate or sodium phosphate at a concentration of 25 mM to 150 mM with a pH of 5.8 to 8.0, (ii) guanidine-HCl at a concentration of 0.3 M to 2 M, (iii) L-Arginine at a concentration of 0.25 M to 1 M, (iv) Tween-80 at a concentration of 0.05% to 1%, and (v) oxidized glutathione at a concentration of 1 mM to 4 mM and reduced glutathione at a concentration of 0.05 mM to 0.8 mM, wherein the ratio of oxidized to reduced glutathione is from 5:1 to 20:1.

In some embodiments, the denatured polypeptide is a polypeptide containing a TGF beta superfamily member.

"TGF beta superfamily member," as used herein, refers to a protein having a sequence identical to a wild type member of the TGF beta superfamily, a truncate that retains the biological activity of the wild type protein, or a variant that has at least 70% sequence identity to the wild type protein (full length or mature protein) and retains the biological activity of the wild type protein. Members of the TGF beta superfamily, include, for example, TGF-betas, growth differentiation factors, bone morphogenetic proteins, activins, inhibins, and glial cell line-derived neurotrophic factors. In some embodiments, a variant has at least 70%, 80%, 85%, 90%, 95%, or 98% sequence identity to the full length wild type protein and retains the biological activity of the wild type protein. In some embodiments, a variant has at least 70%, 80%, 85%, 90%, 95%, or 98% sequence identity to the mature wild type protein and retains the biological activity of the wild type protein.

A description of the concentration of "refolding buffer" components used in the methods described herein refers to the final concentration of the refolding buffer components present in the reaction with the denatured polypeptide (not to the concentration of the components in a stock solution of refolding buffer prior to addition with other components of the folding reaction).

As used herein, "to induce folding of a polypeptide" refers to the induction of a tertiary structure in a polypeptide, and the acquisition of associated biological activity, that corresponds to that of the wild type protein.

The TGF beta superfamily member can be a glial cell line-derived neurotrophic factor (GDNF) family member. "GDNF family member," as used herein, refers to a protein having a sequence identical to a wild type member of the GDNF family, a truncate that retains the biological activity of the wild type protein, or a variant that has at least 70% sequence identity to the wild type protein (full length or mature protein) and retains the biological activity of the wild type protein. Members of the GDNF family include GDNF, neurturin, neublastin, and persephin. In some embodiments, a variant has at least 70%, 80%, 85%, 90%, 95%, or 98% sequence identity to the full length wild type protein and retains the biological activity of the wild type protein. In some embodiments, a variant has at least 70%, 80%, 85%, 90%, 95%, or 98% sequence identity to the mature wild type protein and retains the biological activity of the wild type protein.

In some embodiments, the GDNF family member is a neublastin protein. "A neublastin protein," as used herein, refers to a protein having a sequence identical to a wild type neublastin (e.g., human neublastin), a truncate that retains the biological activity of the wild type protein, or a variant that has at least 70% sequence identity to the wild type protein (full length or mature neublastin protein) and retains the biological activity of the wild type protein. In some embodiments, a variant has at least 70%, 80%, 85%, 90%, 95%, or 98% sequence identity to the full length wild type protein and retains the biological activity of the wild type protein. In some embodiments, a variant has at least 70%, 80%, 85%, 90%, 95%, or 98% sequence identity to the mature wild type protein (e.g., amino acid residues 108-220 of SEQ ID NO:1) and retains the biological activity of the wild type protein. A neublastin protein can, for example, contain or consist of amino acid residues 122-220 of SEQ ID NO:1, amino acid residues 117-220 of SEQ ID NO:1, or amino acid residues 108-220 of SEQ ID NO:1.

The method can further include expressing the polypeptide in bacteria (e.g., E. coli) prior to inducing folding with the refolding buffer. In some embodiments, the polypeptide is expressed in bacteria in an insoluble form and, prior to inducing folding with the refolding buffer, the insoluble polypeptide is contacted with an amount of a solubilization buffer effective to denature the polypeptide.

In some embodiments, the refolding buffer contains L-Arginine at a concentration of 0.30 M to 0.5M. In other embodiments, the refolding buffer contains L-Arginine at a concentration of at least 0.30 M. In other embodiments, the refolding buffer contains L-Arginine at a concentration of at least 0.35 M. In other embodiments, the refolding buffer contains L-Arginine at a concentration of 0.35 M.

In some embodiments, the refolding buffer contains Tween-80 at a concentration of 0.1% to 1%. In other embodiments, the refolding buffer contains Tween-80 at a concentration of 0.1% to 0.5%. In other embodiments, the refolding buffer contains Tween-80 at a concentration of at least 0.1%. In other embodiments, the refolding buffer contains Tween-80 at a concentration of 0.1%.

In some embodiments, the refolding buffer contains oxidized and reduced glutathione at a ratio of from 5:1 to 10:1. In other embodiments, the refolding buffer contains oxidized and reduced glutathione at a ratio of 5:1. In some embodiments, the refolding buffer contains oxidized glutathione at a concentration of 1 mM to 2 mM. In other embodiments, the refolding buffer contains oxidized glutathione at a concentration of 1 mM.

In some embodiments, the refolding buffer contains guanidine-HCl at a concentration of 0.5 M to 1.0 M. In other embodiments, the refolding buffer contains guanidine-HCl at a concentration of at least 0.5 M. In other embodiments, the refolding buffer contains guanidine-HCl at a concentration of 0.5 M.

In some embodiments, the refolding buffer contains potassium phosphate at a concentration of 25 mM to 100 mM. In other embodiments, the refolding buffer contains potassium phosphate at a concentration of 25 mM to 75 mM. In other embodiments, the refolding buffer contains potassium phosphate at a concentration of at least 50 mM. In other embodiments, the refolding buffer contains potassium phosphate at a concentration of 50 mM. In some embodiments, the refolding buffer contains potassium phosphate at a pH of 7.0 to 8.0. In other embodiments, the refolding buffer contains potassium phosphate at a pH of 7.5 to 8.0. In other embodiments, the refolding buffer contains potassium phosphate at a pH of about 7.8.

The refolding buffer can optionally contain or consist of the following components (i) potassium phosphate pH 7.8 at a concentration of 50 mM, (ii) guanidine-HCl at a concentration of 0.5 M, (iii) L-Arginine at a concentration of 0.35 M, (iv) Tween-80 at a concentration of 0.1%, (v) oxidized glutathione at a concentration of 1 mM, and (vi) reduced glutathione at a concentration of 0.2 mM.

In some embodiments, the refolding buffer does not consist of (i) potassium phosphate pH 7.8 at a concentration of 50 mM, (ii) guanidine-HCl at a concentration of 0.5 M, (iii) L-Arginine at a concentration of 0.35 M, (iv) Tween-80 at a concentration of 0.1%, (v) oxidized glutathione at a concentration of 1 mM, and (vi) reduced glutathione at a concentration of 0.2 mM.

In some embodiments, the refolding buffer lacks urea and/or glycine.

In an other aspect, the invention features a composition containing an amount of a refolding buffer effective to, when diluted by a factor of 1 to 10, induce folding of a neublastin polypeptide, wherein the refolding buffer contains the following components at 1 to 10 times the stated concentrations: (i) potassium phosphate or sodium phosphate at a concentration of 25 mM to 150 mM with a pH ranging from 5.8 to 8.0; (ii) guanidine-HCl at a concentration of 0.3 M to 2 M; (iii) L-Arginine at a concentration of 0.25 M to 1 M; (iv) Tween-80 at a concentration of 0.05% to 1%; and (v) oxidized glutathione at a concentration of 1 mM to 4 mM and reduced glutathione at a concentration of 0.05 mM to 0.8 mM, wherein the ratio of oxidized to reduced glutathione is from 5:1 to 20:1. Such a composition can optionally be used as a stock solution that is diluted with other components prior to commencement of a folding reaction.

In some embodiments, the refolding buffer contains L-Arginine at 1 to 10 times a concentration of 0.30 M to 0.5M. In other embodiments, the refolding buffer contains L-Arginine at 1 to 10 times a concentration of at least 0.30 M. In other embodiments, the refolding buffer contains L-Arginine at 1 to 10 times a concentration of at least 0.35 M. In other embodiments, the refolding buffer contains L-Arginine at 1 to 10 times a concentration of 0.35 M.

In some embodiments, the refolding buffer contains Tween-80 at 1 to 10 times a concentration of 0.1% to 1%. In other embodiments, the refolding buffer contains Tween-80 at 1 to 10 times a concentration of 0.1% to 0.5%. In other embodiments, the refolding buffer contains Tween-80 at 1 to 10 times a concentration of at least 0.1%. In other embodiments, the refolding buffer contains Tween-80 at 1 to 10 times a concentration of 0.1%.

In some embodiments, the refolding buffer contains oxidized and reduced glutathione at a ratio of from 5:1 to 10:1. In other embodiments, the refolding buffer contains oxidized and reduced glutathione at a ratio of 5:1. In some embodiments, the refolding buffer contains oxidized glutathione at 1 to 10 times a concentration of 1 mM to 2 mM. In other embodiments, the refolding buffer contains oxidized glutathione at 1 to 10 times a concentration of 1 mM.

In some embodiments, the refolding buffer contains guanidine-HCl at 1 to 10 times a concentration of 0.5 M to 1.0 M. In other embodiments, the refolding buffer contains guanidine-HCl at 1 to 10 times a concentration of at least 0.5 M. In other embodiments, the refolding buffer contains guanidine-HCl at 1 to 10 times a concentration of 0.5 M.

In some embodiments, the refolding buffer contains potassium phosphate at 1 to 10 times a concentration of 25 mM to 100 mM. In other embodiments, the refolding buffer contains potassium phosphate at 1 to 10 times a concentration of 25 mM to 75 mM. In other embodiments, the refolding buffer contains potassium phosphate at 1 to 10 times a concentration of at least 50 mM. In other embodiments, the refolding buffer contains potassium phosphate at 1 to 10 times a concentration of 50 mM. In some embodiments, the refolding buffer contains potassium phosphate at a pH of 7.0 to 8.0. In other embodiments, the refolding buffer contains potassium phosphate at a pH of 7.5 to 8.0. In other embodiments, the refolding buffer contains potassium phosphate at a pH of about 7.8.

The refolding buffer can optionally contain or consist of the following components at 1 to 10 times the stated concentrations: (i) potassium phosphate pH 7.8 at a concentration of 50 mM; (ii) guanidine-HCl at a concentration of 0.5 M; (iii) L-Arginine at a concentration of 0.35 M; (iv) Tween-80 at a concentration of 0.1%; (v) oxidized glutathione at a concentration of 1 mM; and (vi) reduced glutathione at a concentration of 0.2 mM.

In some embodiments, the refolding buffer does not consist of (i) potassium phosphate pH 7.8 at a concentration of 50 mM, (ii) guanidine-HCl at a concentration of 0.5 M, (iii) L-Arginine at a concentration of 0.35 M, (iv) Tween-80 at a concentration of 0.1%, (v) oxidized glutathione at a concentration of 1 mM, and (vi) reduced glutathione at a concentration of 0.2 mM.

In some embodiments, the refolding buffer lacks urea and/or glycine.

The compositions and methods described herein are advantageous in that they allow for the refolding and purification of large quantities of a properly refolded TGF beta superfamily protein, such as neublastin, in circumstances where the protein is produced in a host (e.g., bacteria) that does not yield a properly folded, biologically active product.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

BRIEF DESCRIPTION OF THE DRAWINGS

FIG. 1 depicts the sequences of human and rat 113 amino acid and 104 amino acid forms of neublastin.

DETAILED DESCRIPTION

Figure 2:
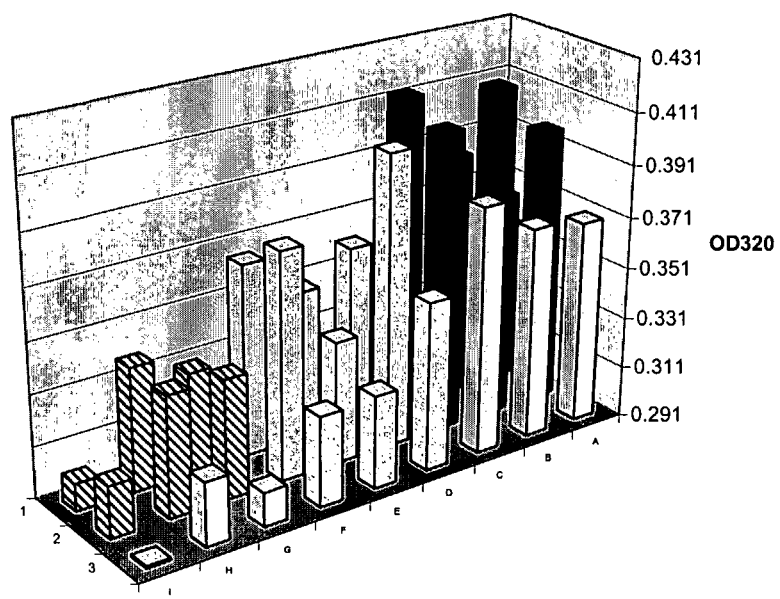
FIG. 2. is a graph depicting absorbance detected following the incubation of solubilized neublastin of the refolding buffers detailed in Table 1 (buffer 4, which contains Tween-80 at a concentration of 1%, is not shown).

The present invention provides compositions and methods for inducing folding of a denatured polypeptide belonging to the TGF beta superfamily. Application of certain compositions to induce the folding of denatured neublastin, a member of the TGF beta superfamily and the GDNF subfamily, is described in the accompanying working examples. Because neublastin has a cysteine knot structure common to members of the TGF beta superfamily and the GDNF subfamily, the refolding buffers described herein are expected to be effective at inducing the folding of other polypeptides belonging to the TGF beta superfamily and the GDNF subfamily.

Neublastin

The native human pre pro neublastin polypeptide is 220 amino acids long and has the following sequence: MELGLGGLSTLSHCPWPRRQPALWPTLAALALLSSV $\overline{\text{A}}$EASLGSAPRSPAPREGPPPVLASPAGHLPGGRTARW CS$\overline{\text{GR}}$ARRPPPQPSRPAPPPPAP PSALPRGGRAARAGG PGSRARAAGARGCRLRSQLVPVRALGLGHRS $\overline{\phantom{X}}$ DELVRFRF CSGSCRRARSPHDLSLASLLGAGALRPP-PGSRPVSQPCCRPTRYEAVSFMDVNST WRTVDRL-SATACGCLG (SEQ ID NO:1).

The human neublastin signal peptide begins with the methionine at position 1 (underlined) and ends with alanine at position 39 (underlined). The full length pro-domain of human neublastin begins with serine at position 40 (underlined) and ends with arginine at position 107 (underlined). Mature human neublastin polypeptide consists of the carboxy terminal 113 amino acids, beginning with alanine at position 108 and ending with glycine at position 220. The compositions and methods described herein provide for efficient folding of a denatured neublastin protein, including full length neublastin, a mature neublastin (lacking the signal peptide and pro domains), or a biologically active truncate or variant of a mature neublastin.

A neublastin protein folded according to the methods described herein can vary in length. Although the mature human neublastin polypeptide can consist of the carboxy terminal 113 amino acids of pre pro neublastin, not all of the 113 amino acids are required to achieve useful neublastin biological activity. Amino terminal truncation is permissible. Thus, a neublastin polypeptide can correspond to the carboxy terminal 99-113 amino acids of native human neublastin (i.e., its length can be 99, 100, 101, 102, 103, 104, 105, 106, 107, 108, 109, 110, 111, 112, or 113 amino acids). Neublastin polypeptides consisting of the carboxy terminal 104 and 113 amino acids of neublastin are exemplified in the working examples provided below.

In addition to varying in length, the neublastin polypeptide can vary in sequence. In particular, certain amino acid substitutions can be introduced into the neublastin sequence without appreciable loss of a neublastin biological activity described herein. In exemplary embodiments, a polypeptide can be at least 70%, 80%, 85%, 90%, 95%, 98% or 99% identical to SEQ ID NO:1 (or 70%, 80%, 85%, 90%, 95%, 98% or 99% identical to amino acids 108-220 of SEQ ID NO:1). A variant neublastin polypeptide differing in sequence from those disclosed in SEQ ID NO:1 (or amino acids 108-220 of SEQ ID NO:1) may include one or more conservative amino acid substitutions, one or more non conservative amino acid substitutions, and/or one or more deletions or insertions. In some embodiments, the variant neublastin polypeptide includes at least one amino acid substitution with respect to SEQ ID NO:1 (or amino acids 108-220 of SEQ ID NO:1), which provides an internal polymer conjugation site to which a polymer (e.g., a polyalkylene glycol moiety such as a polyethylene glycol moiety) can be conjugated (exemplary neublastin variants are described in WO 02/060929, the content of which is incorporated herein by reference). In some embodiments, the variant neublastin polypeptide includes at least one amino acid substitution (e.g., a non-conservative substitution) with respect to SEQ ID NO:1 (or amino acids 108-220 of SEQ ID NO:1), which decreases heparin binding (e.g., R155E, R156E, R158E, or R155, 156E, or one or more of these substitutions at the corresponding position or positions in a mature neublastin polypeptide).

Conservative substitutions typically include the substitution of one amino acid for another with similar characteristics such as substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The non polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution.

A polypeptide used in the methods described herein can contain heterologous amino acid sequences in addition to a neublastin protein. "Heterologous," as used when referring to an amino acid sequence, means a sequence that originates from a source foreign to the particular host cell, or, if from the same host cell, is modified from its original form. Exemplary heterologous sequences include a heterologous signal sequence (e.g., native rat albumin signal sequence, a modified rat signal sequence, or a human growth hormone signal sequence) or a sequence used for purification of a neublastin protein (e.g., a histidine tag).

Neublastin Activity

Neublastin polypeptides used in the methods described herein display at least one biological activity of native neublastin. A biologically active neublastin polypeptide is a polypeptide that, when dimerized, can bind, along with GFRα3, to RET and induce RET dimerization and autophosphorylation. (See e.g. Sanicola et al., 1997, *Proc. Natl. Acad. Sci. USA,* 94:6238). Any method of determining receptor binding and receptor autophosphorylation can be used to evaluate the biological activity the neublastin polypeptide. For example, the KIRA assay described in Example 3 can be used to assess neublastin biological activity. (See also, Sadick et al., 1996, *Anal. Biochem.,* 235(2):207).

Refolding Buffer

In general, the refolding buffer used in the methods described herein includes the following components: (i) potassium phosphate at a concentration of 25 mM to 150 mM; (ii) guanidine-HCl at a concentration of 0.3 M to 2 M; (iii) L-Arginine at a concentration of 0.25 M to 1 M; (iv) Tween-80 at a concentration of 0.05% to 1%; and (v) oxidized glutathione at a concentration of 1 mM to 4 mM and reduced glutathione at a concentration of 0.05 mM to 0.8 mM, wherein the ratio of oxidized to reduced glutathione is from 5:1 to 20:1.

In some embodiments, sodium phosphate at a concentration of 25 mM to 150 mM can be used in place of potassium phosphate. The pH of the sodium phosphate or potassium phosphate used in these methods generally falls in the range of 5.8 to 8.0. In addition, in some embodiments, detergents such as Tween-20 or NP40 can be used in place of Tween-80 at a concentration of 0.05% to 1%.

The effectiveness of a particular refolding buffer at inducing folding of a denatured polypeptide can be evaluated by measuring the absorbance (OD 320) following the incubation of the denatured polypeptide in a particular buffer (see Example 1 and FIG. 2). Absorbance detected in such an assay indicates the presence of precipitated, improperly folded protein. As depicted in Example 2 in the accompanying examples, a low absorbance reading indicates that a buffer is effective at inducing folding of a denatured polypeptide. Biological activity of the folded polypeptide can also be measured by the in vitro and/or in vivo biological assays described herein.

The following are examples of the practice of the invention. They are not to be construed as limiting the scope of the invention in any way.

EXAMPLES

Example 1

Identification of a Neublastin Refolding Buffer

Recombinant neublastin was expressed as a 10 histidine-tagged fusion protein (FIG. 1) in *E. coli* under the control of a T7 promoter. Both human and rat 113 and 104 amino acid forms were derived from their respective constructs (FIG. 1) and were refolded and purified by the methods described herein. The starts of the 113 amino acid and the 104 amino acid forms are each underlined and in boldface text in FIG. 1.

When expressed in *E. coli*, neublastin is contained as an insoluble protein within inclusion bodies (IB). Therefore, neublastin must be isolated from IBs and refolded to obtain a soluble and bioactive product. Inclusion bodies were obtained by lysing *E. coli* expressing neublastin in PBS using a Gaulin press followed by centrifugation. Unless otherwise noted, all centrifugations were performed at 4° C., while all other steps were carried out at room temperature. To obtain the maximum possible yield of properly refolded neublastin, it is advantageous to start with IB pellets that are free of cell debris. To accomplish this, IB pellets were weighed and subjected to further washing in IB wash buffer (20 mM Tris pH 8.5 and 0.5 M EDTA; 8 ml per gram protein). The IB pellet was collected by centrifugation at 15,000×g for 20 minutes, the cloudy supernatant discarded, and washed again in the same buffer containing 2% Triton-X 100 (8 ml per gram protein) to help remove contaminating lipids. A final wash was performed to remove the Tween-80 using wash buffer without detergent (8 ml per gram protein) and the supernatant again was discarded.

A freshly made solubilization buffer (6M guanidine-HCl, 0.05 M potassium phosphate pH 7.8, 0.1 M DTT, and 1.0 mM EDTA) was added to the pellet and mixed well using a polytron mixer. To ensure complete solubilization, the mixture was stirred over night at room temperature. The next day, the solution was clarified by centrifugation at 10,000 rpm for 20 minutes. The supernatant was decanted into a new container, and the remaining insoluble pellet was weighed to allow estimation of recovery. Not all of the protein was solubilized by this process. At this point, the soluble protein was quantitated using a standard Bradford protein assay with BSA in solubilization as a control.

To determine whether certain buffer conditions might result in a high yield of properly refolded neublastin, an array of potential refolding buffers was prepared in a 96 well plate (see Table 1).

TABLE 1

96-Well Plate Refolding Buffer Map

|   |   | A mM | B mM | C mM | D mM | E mM | F mM | G mM | H mM | I mM |
|---|---|---|---|---|---|---|---|---|---|---|
| 1 | Phos (pH7.8) | 50 | 50 | 50 | 50 | 50 | 50 | 50 | 50 | 50 |
|   | Guanidine | 500 | 500 | 500 | 500 | 500 | 500 | 500 | 500 | 500 |
|   | Arginine | 150 | 250 | 350 | 150 | 250 | 350 | 150 | 250 | 350 |
|   | Glutathione Reduced | 0.2 | 0.2 | 0.2 | 0.2 | 0.2 | 0.2 | 0.2 | 0.2 | 0.2 |
|   | Glutathione Oxidized | 1 | 2 | 4 | 1 | 2 | 4 | 1 | 2 | 4 |
|   | Tween-80 | 0 | 0 | 0 | 0 | 0 | 0 | 0 | 0 | 0 |
| 2 | Phos (pH7.8) | 50 | 50 | 50 | 50 | 50 | 50 | 50 | 50 | 50 |
|   | Guanidine | 500 | 500 | 500 | 500 | 500 | 500 | 500 | 500 | 500 |
|   | Arginine | 150 | 250 | 350 | 150 | 250 | 350 | 150 | 250 | 350 |
|   | Glutathione Reduced | 0.2 | 0.2 | 0.2 | 0.2 | 0.2 | 0.2 | 0.2 | 0.2 | 0.2 |
|   | Glutathione Oxidized | 1 | 2 | 4 | 1 | 2 | 4 | 1 | 2 | 4 |
|   | Tween-80 | 0.01 | 0.01 | 0.01 | 0.01 | 0.01 | 0.01 | 0.01 | 0.01 | 0.01 |
| 3 | Phos (pH7.8) | 50 | 50 | 50 | 50 | 50 | 50 | 50 | 50 | 50 |
|   | Guanidine | 500 | 500 | 500 | 500 | 500 | 500 | 500 | 500 | 500 |
|   | Arginine | 150 | 250 | 350 | 150 | 250 | 350 | 150 | 250 | 350 |
|   | Glutathione Reduced | 0.2 | 0.2 | 0.2 | 0.2 | 0.2 | 0.2 | 0.2 | 0.2 | 0.2 |
|   | Glutathione Oxidized | 1 | 2 | 4 | 1 | 2 | 4 | 1 | 2 | 4 |
|   | Tween-80 | 0.1 | 0.1 | 0.1 | 0.1 | 0.1 | 0.1 | 0.1 | 0.1 | 0.1 |
| 4 | Phos (pH7.8) | 50 | 50 | 50 | 50 | 50 | 50 | 50 | 50 | 50 |
|   | Guanidine | 500 | 500 | 500 | 500 | 500 | 500 | 500 | 500 | 500 |
|   | Arginine | 150 | 250 | 350 | 150 | 250 | 350 | 150 | 250 | 350 |
|   | Glutathione Reduced | 0.2 | 0.2 | 0.2 | 0.2 | 0.2 | 0.2 | 0.2 | 0.2 | 0.2 |
|   | Glutathione Oxidized | 1 | 2 | 4 | 1 | 2 | 4 | 1 | 2 | 4 |
|   | Tween-80 | 1 | 1 | 1 | 1 | 1 | 1 | 1 | 1 | 1 |

As shown in Table 1, Guanidine HCl (0.5 M), reduced glutathione (0.2 mM), and potassium phosphate pH 7.8 (50 mM) were held constant throughout the plate, whereas the concentrations of L-Arginine, oxidized glutathione, and Tween-80 were varied. L-Arginine was varied from 0.15 M to 0.35 M (addition of up to 0.8 M L-Arginine worked as well) while oxidized glutathione was varied from 1 to 4 mM. In addition, Tween-80 was varied from 0 to 1%. Because glycine in some cases can substitute for L-Arginine during refolding, a separate plate was prepared that kept all the buffer components the same with the exception of L-Arginine, which was substituted with glycine ranging from 25 to 100 mM.

The final volume of the buffer in each well was 280 μl (reduced glutathione was added fresh from a stock concentration). Twenty microliters of solubilized neublastin was then added to each well at a final concentration of 0.1 mg/ml. The absorbance was monitored over a 48-hour period. Any detected absorbance indicated the presence of precipitated and not properly refolded protein.

The most occurrence of precipitation was observed with wells containing 0.15 M L-Arginine while the least amount of precipitation was observed in wells containing 0.35 M L-Arginine (FIG. 2). Of the wells containing 0.35 M L-Arginine, the best overall results were observed in those wells containing 0.1% Tween-80. The best refolding was observed when a ratio of oxidized to reduced glutathione was 20:1 (but a 5:1 ratio was selected for the further experiments described herein so as to decrease the amount of oxidized glutathione needed in the refolding buffer). Based on these criteria, the refolding buffer system presented in the following examples was used and has provided high yield and properly refolded neublastin. Under all buffer conditions, the replacement of L-Arginine with glycine resulted in neublastin precipitation.

Example 2

Refolding and Purification of Neublastin

The results of the buffer analysis described in Example 1 were applied to prepare the following refolding buffer used in this and the following example: 0.5 M guanidine-HCl, 0.35 M L-Arginine, 50 mM potassium phosphate pH 7.8, 0.2 mM reduced glutathione, 1 mM oxidized glutathione, and 0.1% Tween-80. The refolding buffer was made fresh. Solubilized protein was rapidly diluted into refolding buffer at a final protein concentration of 0.05 to 0.5 mg/ml. On average, 0.1 mg/ml of solubilized neublastin was used. This mixture was incubated at room temperature for at least 48 hours. No stirring was necessary.

Host Cell Contaminant Removal Using Ni-IMAC Chromatography

L-Arginine was diluted from 0.35 M to 0.175 M to avoid leaching of Ni from the IMAC resin. This can be performed using either of the following methods. Arginine can be directly diluted to the proper concentration using 0.5 M guanidine-HCl. Water alone was not used because neublastin may precipitate if the guanidine concentration is not maintained (guanidine-HCl should be maintained in the buffers until the cationic chromatography step described below), resulting in a major loss in product recovery. Since directly diluting the L-Arginine would substantially increase the working volume and increase the amount of guanidine required, the protein was concentrated to $\frac{1}{20}^{th}$ of the original volume using a Millipore tangential flow Pellicon unit. Following concentration, L-Arginine was diluted to 0.175 M using 0.5 M guanidine.

The L-Arginine diluted solution was applied to a Ni-NTA IMAC column that was previously equilibrated in column wash buffer (40 mM imidazole and 0.5 M guanidine HCl) using a flow rate of 50 to 100 ml per minute. Neublastin bound to the Ni-NTA matrix via the histidine tag and no product was observed in the flow through. Following washing with five column volumes of wash buffer, neublastin was eluted from the resin using 0.2 M imidazole in 0.5 M guanidine. The column wash buffer (which did not contain neublastin) was discarded. Protein recovery was monitored using a Bradford assay. In addition, host cell contaminants were monitored from this point onward.

Histidine Tag Separation from Neublastin by Protease Digestion

One of two possible histidine tag removal procedures was employed, depending on the length of neublastin required (113 amino acids or 104 amino acids).

To generate the wild-type 113 amino acid neublastin product, Endo Lys C was used to clip the tag c-terminal of the lysine residue contained within the tag. Five units of Endo Lys C (WAKO, catalogue #129-02541) per gram of neublastin were added to the material from the Ni-NTA elution. No buffer substitution or pH adjustment was necessary (in some cases buffer substitution using 10 mM Hepes pH 7.8 was used and worked effectively). Neublastin with protease was incubated over night at room temperature with constant stirring.

To generate the 104 amino acid form of neublastin, the histidine-tagged product was treated with trypsin (Cooper Biomedical #3740) using a 1:2000 ratio of trypsin to neublastin. Again, no buffer substitution or pH adjustment was necessary. The mixture was incubated over night at room temperature with constant stirring.

Ni-NTA resin was equilibrated with wash buffer (0.5 M guanidine-HCl and 0.04 M imidazole). Following adjustment of the imidazole concentration within the neublastin preparation to 0.04 M from 0.2 M using 0.5 M guanidine-HCl, the material was applied to the Ni-NTA resin with a 50 to 100 ml per minute flow rate. The column flow through which contained non-tagged neublastin was collected and monitored for neublastin using the Bradford assay. To re-generate the Ni-NTA resin, the histidine tag was eluted using 0.2 M imidazole in 0.5 M guanidine HCl. This material was subjected to SDS/PAGE along with the resin flow through to establish the efficiency of the protease digestion.

The Ni-NTA flow through from the previous step was adjusted to 0.35 M guanidine-HCl by the addition of ddH$_2$O. Higher concentrations of guanidine may prevent neublastin from binding to the cationic matrix. A C-100 filter-binding cartridge (Sartorious, catalogue # C100X) was equilibrated with C-100 wash buffer (5 mM sodium phosphate pH 6.5 and 0.35 M NaCl).

SP-Sepharose (AmershamPharmacia) can substitute for C-100 membrane filters. However, C-100 was chosen due to its increased surface area compared to that of classical column chromatography. When purifying neublastin on SP-Sepharose, local aggregation of neublastin can be prevented by choosing a larger column diameter and/or lowering protein load. This prevents high local concentrations of neublastin which can contribute to tetramer formation and product precipitation, especially when using sodium phosphate buffer.

Neublastin in 0.35 M guanidine-HCl was applied to the C-100 filter at a flow rate of 50 to 100 ml per minute followed by extensive washing of the filter with C-100 wash buffer. This step removes any remaining histidine tag, endotoxin, and neublastin monomer. Neublastin dimer was recovered by eluting the protein from the C-100 matrix using 5 mM sodium phosphate pH 6.5 and 1 M sodium chloride. The elution was monitored by UV absorption at 280 nm and the neublastin peak collected in one container.

Neublastin Concentration and Buffer Substitution

Neublastin was concentrated by Millipore Biomax-10 tangential flow filtration and diafiltered with the same unit to 5 mM sodium phosphate pH 6.5 and 0.15 M sodium chloride with 5 diafiltration volumes. An effort was made to aim for 1.0-1.5 mg/ml final protein concentration, and not permit the concentration go above 2.0 mg/ml, otherwise neublastin may begin to precipitate in this formulation with a large protein loss. Once the product was concentrated to 1.0 mg/ml and formulated in 5 mM sodium phosphate pH 6.5 and 0.15 M sodium chloride, neublastin was aliquoted into convenient sizes and stored at −70° C. until needed.

Example 3

Analytical Characterization of Neublastin

Purified neublastin described in Example 2 was subjected to various analytical tests to verify purity, primary amino acid sequence, bioactivity, and disulfide structural integrity.

SDS/PAGE Estimation of Purity and Molecular Weight

Samples, taken from each of the neublastin refolding/purification steps, were subjected to SDS/PAGE analysis through a 4 to 20% acrylamide gel under non-reducing conditions. The final neublastin product migrated as a reducible dimer of 24,000 Da with an estimated purity of >98%.

Mass Spectrometry of Refolding Rat Neublastin

To estimate the purity and to determine mass of the product refolded, neublastin was subjected to mass spectrometry on a ZMD mass spectrometer. Neublastin was denatured in 8M urea and treated with DTT prior to analysis to reduce all disulfide bonds and convert the dimer molecule into monomer. The major signal identified represents rat neublastin residues 10 to 113 suggesting the predominant species in the preparation is as expected. However, a major signal at 10991 Da was identified and is predicted to correspond to a Leucine deletion, and a signal at 11076 is predicted to be a small amount of an Arginine to Lysine substitution. The low level peaks correspond to oxidation, acetonitrile adducts and TFA adducts. A small amount of the 106 amino acid form of neublastin was also identified. No trypsin-associated peaks were identified.

Characterization of Rat 104 Amino Acid Neublastin by AspN Peptide Mapping

AspN peptide mapping was carried out on neublastin that was produced by trypsin digestion to remove the histidine tag. This batch was compared to several other neublastin preparations including the wild-type rat 113 amino acid, wild-type human 113 amino acid, human 104 amino acid forms. Results demonstrated that this batch was as predicted, with approximately 8% oxidation at Met92, 5% Leu61 deletion, low levels of Arg to Lys mutations and less than 1% deamidation at Asn95.

Disulfide Analysis of Rat 104 Amino Acid Neublastin

Disulfide analysis was carried out on rat 104 amino acid neublastin. Wild-type rat 113 amino acid neublastin was run in parallel as a reference. Approximately 150 μL of refolded and purified neublastin was used for disulfide mapping. Results demonstrated that all disulfide linkages in the two samples are comparable and as expected. The profile of the neublastin monomer is similar to that of the reference, except for the area under low-level peaks eluting just ahead of the main monomer peak. These earlier-eluting peaks are predicted to contain, in part, oxidized monomer and were not included in down-stream mass mapping. Fractions containing disulfide-linked peptides were pooled and analyzed by MALDI-TOF mass spectrometry using DHB as the matrix. The data indicated that rat 104 amino acid neublastin following AspN/trypsin digestion is as predicted, and there is no evidence of mixed disulfide connectivity.

Assay of Neublastin Activity Using the Kinase Receptor Activation-Enzyme-Linked Immunosorbant Neublastin activity was determined by its ability to stimulate c-Ret phosphorylation in NB41A3-mRL3 cells, an adherent murine neuroblastoma cell line that expresses Ret and GFRa3. NB41A3-mRL3 cells were plated in DMEM supplemented with 10% FBS at 2×105 cells per well in 24-well plates, and cultured for 18 hours at 37° C. and 5% $CO_2$. Following removal of the media and a cell wash with 1 ml of PBS per well, the cells were stimulated with DMEM containing either 113 amino acid or 104 amino acid neublastin for 10 minutes at 37° C. and 5% $CO_2$. To stop neublastin activity, the media was removed and the cells washed with PBS immediately before lysis with 10 mM Tris, pH 8.0, 0.5% NP40, 0.2% DOC, 50 mM NaF, 0.1 mM $Na_3VO_4$, and 1 mM PMSF. After a 1-hour incubation at 4° C., the lysates were agitated by repeated pipetting and transferred (0.25 ml per well) to a 96-well ELISA plate coated with anti-RET mAb (AA.GE7.3). The wells were blocked at room temperature for 1 hour with blocking buffer (TBST containing 1% normal mouse serum and 3% BSA) followed by six washes with TBST alone. Phosphorylated RET was detected by incubating (2 hours) the captured receptor with HRP-conjugated phosphotyrosine antibody (4G10; 0.2 μg per well). Following the incubation, the wells were washed six times with TBST, and the HRP activity detected at 450 nm with a colorimetric assay. The absorbance values from wells treated with lysate or with lysis buffer alone were measured, background corrected, and the data plotted as a function of the concentration of neublastin present in the activation mixture. Rat 104 amino acid neublastin was as active in the KIRA assay as was the positive 113 amino acid neublastin control demonstrating that the refolding/purification process yields biologically active product.

Endotoxin Assay

Using the Limulus Amebocyte Lysate assay and manufacturer-suggested conditions (Bio*Whittaker), endotoxin levels in each of the purification steps were determined. The vast majority of the endotoxin is removed during the first Ni-NTA wash step. Following the addition of trypsin, it was observed that the endotoxin level went up slightly which most likely is due to endotoxin in the trypsin preparation used. Washing the C100 column with a large amount of wash buffer appears to be useful to remove remaining endotoxin. Endotoxin levels within the final product were well below maximum acceptable levels.

Host Cell Protein Assay

Using an *E. coli* host cell protein assay kit from Cygnus Technologies and manufacturer-suggested conditions, host cell protein contamination was monitored in each of the purification steps. This kit is an ELISA-based assay that is sensitive down to 1 ng/ml host cell protein. As with the endotoxin result above, most of the host protein clearance occurs during the first Ni-NTA chromatography as well as during the C100 washing. Host cell protein was determined to be less than 0.0001% of the final product.

Trypsin Clearance Assay

Trypsin clearance was monitored using a fluorescence-based assay using N-T-BOC-GLN-ALA-ARG 7-AMIDO-4-Methylcoumarin HCl as substrate and was sensitive down to less than 40 ng/ml. Most, if not all, of the added trypsin was removed by the C100 flow through wash. The amount of trypsin remaining in the final product was less than 0.004% (below the level of sensitivity).

Histidine-Tag Detection ELISA

A histidine tag ELISA using an anti-polyhistidine antibody was developed to monitor histidine-tagged neublastin remaining in the final preparation. As expected, the majority of the histidine tag was found in the material prior to the first Ni-NTA and none was in the first Ni-NTA flow through, indicating that the majority of the histidine-tagged neublastin bound the Ni-NTA resin. This material eluted from the resin with the 0.2 M imidazole elution. The sensitivity of this assay was approximate 0.3 μg/ml, and the final amount of histidine-tagged neublastin identified in the final product was determined to be 0.12% of the total protein or 0.88 mg.

Host Cell DNA Detection Assay

Clearance of host cell DNA was monitored using an assay that utilizes single-stranded DNA binding protein coupled to avidin in an ELISA-based sandwich assay. This assay was demonstrated to be sensitive to approximately 200 pg/ml of *E. coli* DNA. Based on the single-stranded DNA binding assay, the final neublastin preparation was determined to have less than 0.0001% contaminating host cell DNA. As with other assays described above, both the first Ni-NTA chromatography step and the C100 wash step were most efficient at removing the DNA impurities within the starting material.

Chronic Constriction Injury (CCI) Rats Treated with 104 Amino Acid Neublastin

Neublastin treated CCI rats displayed diminished tactile allodynia as compared to vehicle treated controls. The neublastin treated rats were able to withstand a greater force applied to the ipsilateral foot. Tactile allodynia was evaluated with von Frey Hairs applying the up-down method (Chaplan et al., 1994). Rats were tested at days 7, 10, 14, 17, and 21 for altered nociceptive thresholds. Shams (n=3) did not display a different gram threshold during the testing period, while all CCI rats had a lower threshold for the applied von Frey Hairs compared to their baseline values. Neublastin-104 1 mg/Kg (n=8) and 3 mg/Kg (n=7) treated rats were able to withstand an elevated threshold compared to the vehicle treated controls (n=8). The force withstood by neublastin treated animals was statically significant ($p<0.05$) at days 17 and 21 post-op CCI. Thermal hyperalgesia was attenuated in the neublastin treated CCI rats, with the 3 mg/Kg dose demonstrating a higher efficacy than the 1 mg/Kg dose at day 21 post-op. Thermal hyperalgesia was determined using a Hargreaves device to assess thermal withdrawal latency. Rats were tested at days 7, 10, 14, 17, and 21 for lowered paw withdrawal latencies. Shams (n=3) did not display altered paw withdrawal latency during the testing period, while all CCI rats had a shorter paw withdrawal latency compared to their baseline values. Neublastin-104 1 mg/Kg (n=8) and 3 mg/Kg (n=7) were able to withstand longer application of the thermal stimulus compared to the vehicle treated controls (n=8) at days 14, 16 and 21 following CCI induction. While the 104 amino acid neublastin 3 mg/Kg-treated rats demonstrated a significantly higher latency on day 21 post-op compared to the 104 amino acid neublastin 1 mg/Kg treated rats, the duration of paw withdrawal latency by neublastin treated animals was statically significant ($p<0.05$) at days 14, 17, and 21 post-op CCI.

CCI rats treated with neublastin were able to apply more weight to the affected chronic constricted hindlimb as seen with the incapacitance test. Incapacitance was determined using an incapacitance meter to assess the weight distribution of each foot. At baseline, rats distributed equal weight between their feet, but following injury there was less weight applied to the ipsilateral foot. Shams (n=4) did not display altered weight distribution between their feet during the testing period, while all CCI rats applied less weight to the affected foot compared to their baseline values. 104 amino acid neublastin 1 mg/Kg (n=8) and 3 mg/Kg (n=7) applied more weight to the ipsilateral foot as compared to the vehicle treated controls (n=8). The incapacitance of the affected foot in neublastin treated animals was statically significant ($p<0.05$) at days 14, 17, and 21 post-op CCI.

While there was not a statistically significant difference between the neublastin and vehicle treated CCI rats on the cold allodynia test, the neublastin-treated rats tended to have shorter durations on day 10. Cold allodynia was determined using a copper cold plate chilled to 4° C. for a 5 minute testing period. Rats were tested at days 7, 10, 14, 17, and 21 for elevated paw withdrawal duration compared to their baseline values. At baseline, no animals reacted to the cold. Shams (n=3) did not display elevated paw withdrawal duration throughout the testing period, while both all CCI rats had increased paw withdrawal duration compared to their baseline values. 104 amino acid neublastin 1 mg/Kg (n=8) and 3 mg/Kg (n=7)) elevated the affected paw for a shorter period of time compared to the vehicle treated controls (n=8) at days 14, 17, and 21 following CCI induction, although the duration of paw withdrawal by neublastin treated animals was not statically significant.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A composition comprising an amount of a refolding buffer effective to, when diluted by a factor of 1 to 10, induce folding of a neublastin polypeptide, wherein the refolding buffer comprises the following components at 1 to 10 times the stated concentrations: (i) potassium phosphate or sodium phosphate at a concentration of 25 mM to 150 mM with a pH ranging from 5.8 to 8.0; (ii) guanidine-HCl at a concentration of 0.3 M to 2 M; (iii) L-Arginine at a concentration of 0.25 M to 1 M; (iv) Tween-80 at a concentration of 0.05% to 1%; and (v) oxidized glutathione at a concentration of 1 mM to 4 mM and reduced glutathione at a concentration of 0.05 mM to 0.8 mM, wherein the ratio of oxidized to reduced glutathione is from 5:1 to 20:1.

2. The composition of claim 1, wherein the refolding buffer comprises L-Arginine at 1 to 10 times a concentration of 0.30 M to 0.5M.

3. The composition of claim 1, wherein the refolding buffer comprises L-Arginine at 1 to 10 times a concentration of at least 0.30 M.

4. The composition of claim 1, wherein the refolding buffer comprises L-Arginine at 1 to 10 times a concentration of at least 0.35 M.

5. The composition of claim 1, wherein the refolding buffer comprises L-Arginine at 1 to 10 times a concentration of 0.35 M.

6. The composition of claim 1, wherein the refolding buffer comprises Tween-80 at 1 to 10 times a concentration of 0.1% to 1%.

7. The composition of claim 1, wherein the refolding buffer comprises Tween-80 at 1 to 10 times a concentration of 0.1% to 0.5%.

8. The composition of claim 1, wherein the refolding buffer comprises Tween-80 at 1 to 10 times a concentration of at least 0.1%.

9. The composition of claim 1, wherein the refolding buffer comprises Tween-80 at 1 to 10 times a concentration of 0.1%.

10. The composition of claim 1, wherein the refolding buffer comprises oxidized and reduced glutathione at a ratio of from 5:1 to 10:1.

11. The composition of claim 1, wherein the refolding buffer comprises oxidized and reduced glutathione at a ratio of 5:1.

12. The composition of claim 1, wherein the refolding buffer comprises oxidized glutathione at 1 to 10 times a concentration of 1 mM to 2 mM.

13. The composition of claim 1, wherein the refolding buffer comprises oxidized glutathione at 1 to 10 times a concentration of 1 mM.

14. The composition of claim 1, wherein the refolding buffer comprises guanidine-HCl at 1 to 10 times a concentration of 0.5 M to 1.0 M.

15. The composition of claim 1, wherein the refolding buffer comprises guanidine-HCl at 1 to 10 times a concentration of at least 0.5 M.

16. The composition of claim 1, wherein the refolding buffer comprises guanidine-HCl at 1 to 10 times a concentration of 0.5 M.

17. The composition of claim 1, wherein the refolding buffer comprises potassium phosphate at 1 to 10 times a concentration of 25 mM to 100 mM.

18. The composition of claim 1, wherein the refolding buffer comprises potassium phosphate at 1 to 10 times a concentration of 25 mM to 75 mM.

19. The composition of claim 1, wherein the refolding buffer comprises potassium phosphate at 1 to 10 times a concentration of at least 50 mM.

20. The composition of claim 1, wherein the refolding buffer comprises potassium phosphate at 1 to 10 times a concentration of 50 mM.

21. The composition of claim 1, wherein the refolding buffer comprises potassium phosphate at a pH of 7.0 to 8.0.

22. The composition of claim 1, wherein the refolding buffer comprises potassium phosphate at a pH of 7.5 to 8.0.

23. The composition of claim 1, wherein the refolding buffer comprises potassium phosphate at a pH of about 7.8.

24. The composition of claim 1, wherein the refolding buffer does not consist of (i) potassium phosphate pH 7.8 at a concentration of 50 mM, (ii) guanidine-HCl at a concentration of 0.5 M, (iii) L-Arginine at a concentration of 0.35 M, (iv) Tween-80 at a concentration of 0.1%, (v) oxidized glutathione at a concentration of 1 mM, and (vi) reduced glutathione at a concentration of 0.2 mM.

25. The composition of claim 1, wherein the refolding buffer comprises the following components at 1 to 10 times the stated concentrations: (i) potassium phosphate pH 7.8 at a concentration of 50 mM; (ii) guanidine-HCl at a concentration of 0.5 M; (iii) L-Arginine at a concentration of 0.35 M; (iv) Tween-80 at a concentration of 0.1%; (v) oxidized glutathione at a concentration of 1 mM; and (vi) reduced glutathione at a concentration of 0.2 mM.

26. The composition of claim 1, wherein the refolding buffer consists of the following components at 1 to 10 times the stated concentrations: (i) potassium phosphate pH 7.8 at a concentration of 50 mM; (ii) guanidine-HCl at a concentration of 0.5 M; (iii) L-Arginine at a concentration of 0.35 M; (iv) Tween-80 at a concentration of 0.1%; (v) oxidized glutathione at a concentration of 1 mM; and (vi) reduced glutathione at a concentration of 0.2 mM.

27. The composition of claim 1, wherein the refolding buffer lacks urea.

28. The composition of claim 1, wherein the refolding buffer lacks glycine.

* * * * *

SEQUENCE LISTING

<160> NUMBER OF SEQ ID NOS: 3

<210> SEQ ID NO 1
<211> LENGTH: 220
<212> TYPE: PRT
<213> ORGANISM: Homo sapiens

<400> SEQUENCE: 1

```
Met Glu Leu Gly Leu Gly Gly Leu Ser Thr Leu Ser His Cys Pro Trp
1               5                   10                  15

Pro Arg Arg Gln Pro Ala Leu Trp Pro Thr Leu Ala Ala Leu Ala Leu
                20                  25                  30

Leu Ser Ser Val Ala Glu Ala Ser Leu Gly Ser Ala Pro Arg Ser Pro
            35                  40                  45

Ala Pro Arg Glu Gly Pro Pro Pro Val Leu Ala Ser Pro Ala Gly His
        50                  55                  60

Leu Pro Gly Gly Arg Thr Ala Arg Trp Cys Ser Gly Arg Ala Arg Arg
65                  70                  75                  80

Pro Pro Pro Gln Pro Ser Arg Pro Ala Pro Pro Pro Ala Pro Pro
                85                  90                  95

Ser Ala Leu Pro Arg Gly Gly Arg Ala Ala Arg Ala Gly Gly Pro Gly
                100                 105                 110

Ser Arg Ala Arg Ala Ala Gly Ala Arg Gly Cys Arg Leu Arg Ser Gln
            115                 120                 125

Leu Val Pro Val Arg Ala Leu Gly Leu Gly His Arg Ser Asp Glu Leu
    130                 135                 140

Val Arg Phe Arg Phe Cys Ser Gly Ser Cys Arg Arg Ala Arg Ser Pro
145                 150                 155                 160

His Asp Leu Ser Leu Ala Ser Leu Leu Gly Ala Gly Ala Leu Arg Pro
                165                 170                 175

Pro Pro Gly Ser Arg Pro Val Ser Gln Pro Cys Cys Arg Pro Thr Arg
            180                 185                 190

Tyr Glu Ala Val Ser Phe Met Asp Val Asn Ser Thr Trp Arg Thr Val
        195                 200                 205

Asp Arg Leu Ser Ala Thr Ala Cys Gly Cys Leu Gly
    210                 215                 220
```

<210> SEQ ID NO 2
<211> LENGTH: 135
<212> TYPE: PRT
<213> ORGANISM: Homo sapiens

<400> SEQUENCE: 2

Met Gly His His His His His His His His His His Ser Ser Gly His

```
                1               5                   10                  15
Ile Asp Asp Asp Lys Ala Gly Gly Pro Gly Ser Arg Ala Arg Ala
                    20                  25                  30

Ala Gly Ala Arg Gly Cys Arg Leu Arg Ser Gln Leu Val Pro Val Arg
                    35                  40                  45

Ala Leu Gly Leu Gly His Arg Ser Asp Glu Leu Val Arg Phe Arg Phe
        50                  55                  60

Cys Ser Gly Ser Cys Arg Arg Ala Arg Ser Pro His Asp Leu Ser Leu
65                      70                  75                  80

Ala Ser Leu Leu Gly Ala Gly Ala Leu Arg Pro Pro Gly Ser Arg
                    85                  90                  95

Pro Val Ser Gln Pro Cys Cys Arg Pro Thr Arg Tyr Glu Ala Val Ser
                    100                 105                 110

Phe Met Asp Val Asn Ser Thr Trp Arg Thr Val Asp Arg Leu Ser Ala
                    115                 120                 125

Thr Ala Cys Gly Cys Leu Gly
        130                 135

<210> SEQ ID NO 3
<211> LENGTH: 135
<212> TYPE: PRT
<213> ORGANISM: Rattus norvegicus

<400> SEQUENCE: 3

Met Gly His His His His His His His His His Ser Ser Gly His
 1               5                   10                  15

Ile Asp Asp Asp Lys Ala Gly Thr Arg Ser Ser Arg Ala Arg Ala
                    20                  25                  30

Thr Asp Ala Arg Gly Cys Arg Leu Arg Ser Gln Leu Val Pro Val Ser
                    35                  40                  45

Ala Leu Gly Leu Gly His Ser Ser Asp Glu Leu Ile Arg Phe Arg Phe
        50                  55                  60

Cys Ser Gly Ser Cys Arg Arg Ala Arg Ser Pro His Asp Leu Ser Leu
65                      70                  75                  80

Ala Ser Leu Leu Gly Ala Gly Ala Leu Arg Ser Pro Pro Gly Ser Arg
                    85                  90                  95

Pro Ile Ser Gln Pro Cys Cys Arg Pro Thr Arg Tyr Glu Ala Val Ser
                    100                 105                 110

Phe Met Asp Val Asn Ser Thr Trp Arg Thr Val Asp His Leu Ser Ala
                    115                 120                 125

Thr Ala Cys Gly Cys Leu Gly
        130                 135
```